(12) United States Patent
Kim et al.

(10) Patent No.: US 8,134,035 B2
(45) Date of Patent: Mar. 13, 2012

(54) PREPARATION OF ASYMMETRIC ANTHRACENE DERIVATIVES AND ORGANIC ELECTROLUMINESCENT DEVICE USING SAME

(75) Inventors: Tae-Hyung Kim, Yongin-si (KR); Kyoung-Soo Kim, Daejon (KR)

(73) Assignee: Doosan Corporation, Seoul (KR)

( * ) Notice: Subject to any disclaimer, the term of this patent is extended or adjusted under 35 U.S.C. 154(b) by 0 days.

(21) Appl. No.: 12/992,238

(22) PCT Filed: May 14, 2009

(86) PCT No.: PCT/KR2009/002550
§ 371 (c)(1),
(2), (4) Date: Nov. 11, 2010

(87) PCT Pub. No.: WO2009/139579
PCT Pub. Date: Nov. 19, 2009

(65) Prior Publication Data
US 2011/0065924 A1 Mar. 17, 2011

(30) Foreign Application Priority Data

May 14, 2008 (KR) .................. 10-2008-0044369

(51) Int. Cl.
*C07C 1/207* (2006.01)
(52) U.S. Cl. ........................................ 585/320; 585/469
(58) Field of Classification Search .................. 585/320, 585/469
See application file for complete search history.

(56) References Cited

U.S. PATENT DOCUMENTS
5,232,635 A 8/1993 Van Moer et al.

FOREIGN PATENT DOCUMENTS
| KR | 10-2004-0013377 A | 2/2004 |
| KR | 10-2005-0058465 A | 6/2005 |
| KR | 10-207-0101722 A | 10/2007 |

*Primary Examiner* — Thuan Dinh Dang
(74) *Attorney, Agent, or Firm* — Sughrue Mion, PLLC

(57) ABSTRACT

Provided is a method of preparing asymmetric anthracene derivative, more particularly, a method for high-yield production of an anthracene derivative in which an alkyl group, a cycloalkyl group, a heterocycloalkyl group, an aryl group or a heteroaryl group is introduced at position 2 of anthracene, and an aryl group or a heteroaryl group is introduced at each of positions 9 and 10 of the anthracene.

3 Claims, 3 Drawing Sheets

PREPARATION OF ASYMMETRIC ANTHRACENE DERIVATIVES AND ORGANIC ELECTROLUMINESCENT DEVICE USING SAME

TECHNICAL FIELD

The present invention relates to a novel method of preparing an asymmetric anthracene derivative and a method of manufacturing an organic light-emitting device (OLED) using the same. More particularly, the present invention relates to a method for high-yield production of an anthracene derivative in which an alkyl group, a cycloalkyl group, a heterocycloalkyl group, an aryl group or a heteroaryl group is introduced at position 2 of anthracene, and an aryl group or a heteroaryl group is introduced at each of positions 9 and 10 of the anthracene, and the development of OLEDs with excellent efficiency and lifetime, using the anthracene derivative as a light-emitting material, a hole injection and/or transport material, or an electron transport and/or injection material.

BACKGROUND ART

Anthracene has been known to be potential materials forming organic material layers of organic light-emitting devices (OLEDs) since the 1960s. Anthracene exhibits relatively good effects in view of emission efficiency, lifetime, color purity, etc., but there is still much room for improvement. Thus, many studies have been conduced for improving anthracenes.

For example, a thin film formed by depositing anthracene on an ITO substrate easily undergoes crystallization. In view of this problem, a method of introducing a substituent at position 2 of anthracene has been proposed to break the symmetry of anthracenes, thereby preventing the crystallization of anthracenes, and thus ensuring good film performance.

Further, a method of introducing an aryl group at positions 9 and 10 of anthracene has been also proposed to thereby improve electrical performance. In addition, a method of introducing different aryl groups at positions 9 and 10 of anthracene has also been proposed to increase a dipole moment of an anthracene molecule, thereby leading to improved electrical performance.

In order to improve the emission efficiency, lifetime and color purity of OLEDs, it is necessary to develop anthracene derivatives in which an alkyl group, a cycloalkyl group, a heterocycloalkyl group, an aryl group or a heteroaryl group is introduced at position 2 of anthracene, and an aryl group or a heteroaryl group is introduced at each of positions 9 and 10 of the anthracene. In particular, from an economical point of view, it is necessary to develop a method for high-yield production of the above-described anthracene derivatives.

DETAILED DESCRIPTION OF THE INVENTION

Technical Goal of the Invention

The present invention provides a method for high-yield production of an anthracene derivative in which an alkyl group, a cycloalkyl group, a heterocycloalkyl group, an aryl group or a heteroaryl group is introduced at position 2 of anthracene, and an aryl group or a heteroaryl group is introduced at each of positions 9 and 10 of the anthracene.

Structure and Operation of the Invention

According to an aspect of the present invention, there is provided a method of preparing an anthracene derivative represented by Formula 5, the method including:

(a) reacting a compound of Formula 1 below with a compound of Formula 2 below to obtain a compound of Formula 3 below;

(b) cyclizing the compound of Formula 3 to obtain a compound of Formula 4 below; and (c) introducing an aryl group at position 10 of anthracene of the compound of Formula 4.

[Formula 1]

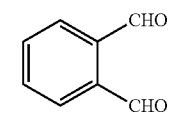

[Formula 2]

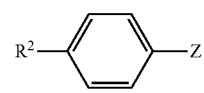

[Formula 3]

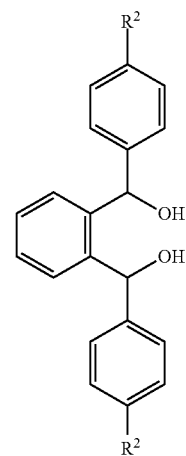

[Formula 4]

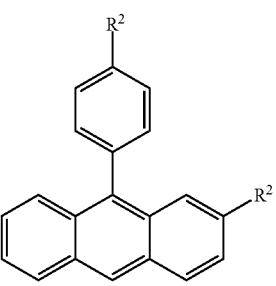

[Formula 5]

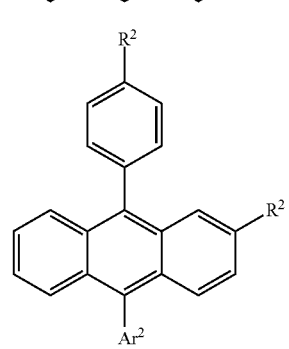

wherein Z is MgX where X is halogen, Li, or Na, $R^2$ is an alkyl group of $C_1$~$C_{30}$, a cycloalkyl group of $C_5$~$C_{30}$, a heterocycloalkyl group of $C_5$~$C_{30}$, an aryl group of $C_5$~$C_{30}$, or a heteroaryl group of $C_5$~$C_{30}$; $Ar^2$ is an aryl group of $C_5$~$C_{30}$ or a heteroaryl group of $C_5$~$C_{30}$; and wherein the alkyl group, cycloalkyl group, heterocycloalkyl group, aryl group and heteroaryl group may be each independently substituted by at least one selected from the group consisting of $C_1$-$C_{30}$ alkyl, $C_2$-$C_{30}$ alkenyl, $C_2$-$C_{30}$ alkynyl, $C_5$-$C_{30}$ aryl, $C_5$-$C_{30}$ heteroaryl, $C_5$-$C_{30}$ aryloxy, $C_1$-$C_{30}$ alkyloxy, $C_5$-$C_{30}$ arylamino, $C_5$-$C_{30}$ diarylamino, $C_5$-$C_{30}$ arylalkyl, $C_5$-$C_{30}$ cycloalkyl, $C_5$-$C_{30}$ heterocycloalkyl and a halogen atom.

Effect of the Invention

According to the present invention, an anthracene derivative with excellent emission efficiency can be produced at high yield, thereby enabling economically effective fabrication of OLEDs.

BEST MODE FOR CARRYING OUT THE INVENTION

Figure 1:
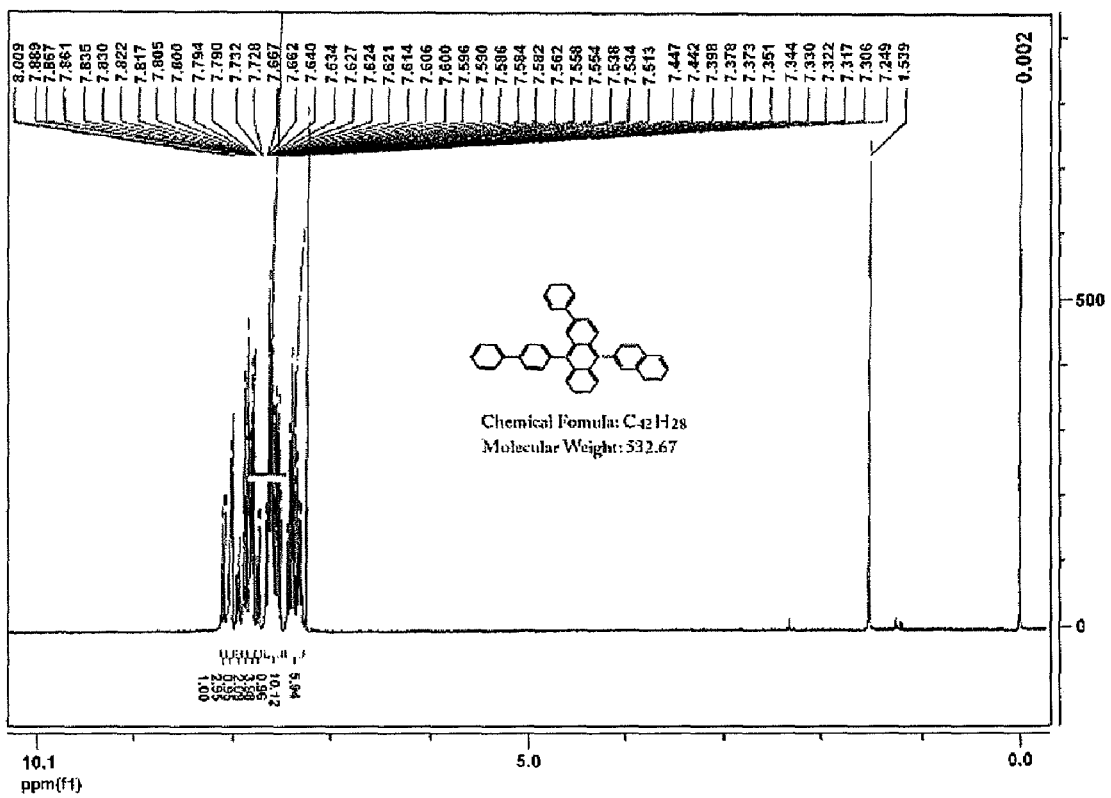
FIG. 1 is an NMR spectrum for an anthracene derivative (Cpd 1) of Example 1.
Figure 1:
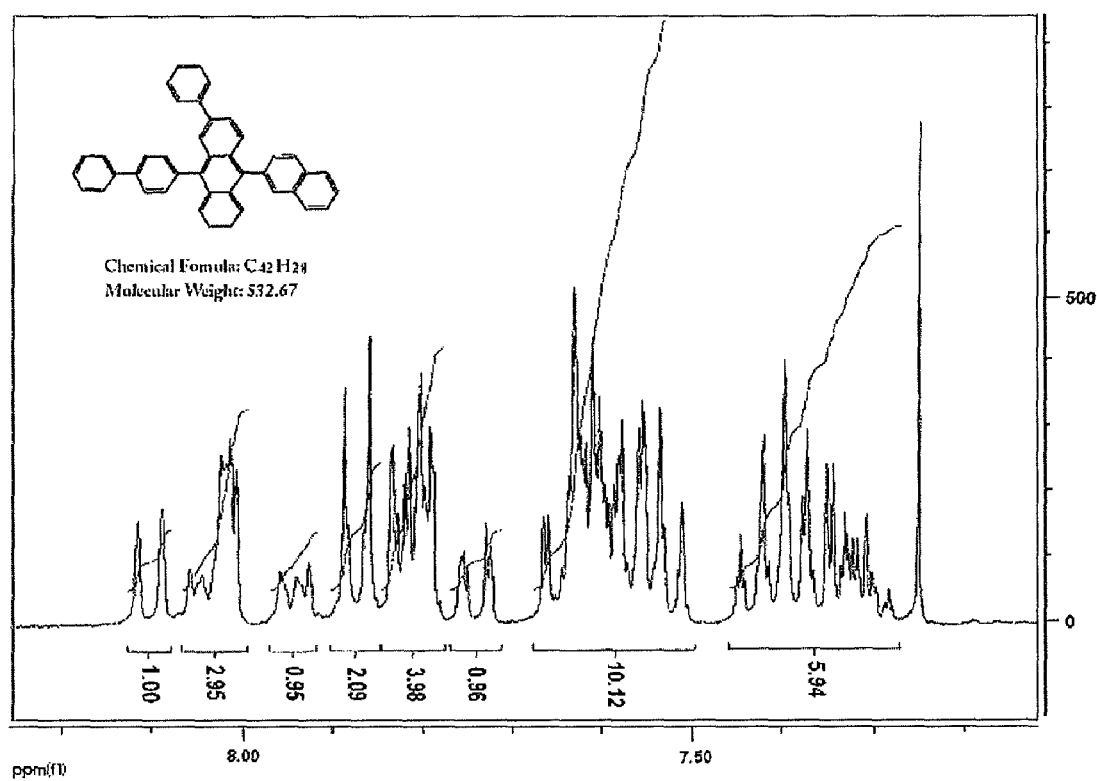

A compound sought to be prepared in the present invention may be an anthracene derivative (hereinafter, referred to as "target anthracene derivative") represented by Formula 6 below in which an alkyl group, a cycloalkyl group, a heterocycloalkyl group, an aryl group or a heteroaryl group is introduced at position 2 of anthracene, and an aryl group or a heteroaryl group is introduced at each of positions 9 and 10 of the anthracene.

[Formula 6]

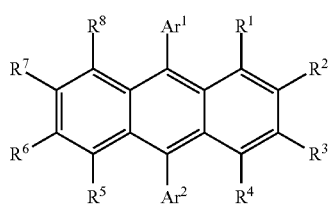

wherein $Ar^1$ and $Ar^2$ are each independently an aryl group of $C_5$~$C_{30}$ or a heteroaryl group of $C_5$~$C_{30}$; $R^2$ is an alkyl group of $C_1$~$C_{30}$, a cycloalkyl group of $C_5$~$C_{30}$, a heterocycloalkyl group of $C_5$~$C_{30}$, an aryl group of $C_5$~$C_{30}$, or a heteroaryl group of $C_5$~$C_{30}$; $R^1$ and $R^3$~$R^8$ are each independently selected from the group consisting of hydrogen, a halogen atom, an alkyl group of $C_1$~$C_{30}$, a cycloalkyl group of $C_5$~$C_{30}$, an alkoxy group of $C_1$~$C_{30}$, a heterocycloalkyl group of $C_5$~$C_{30}$, an aryl group of $C_5$~$C_{30}$, and a heteroaryl group of $C_5$~$C_{30}$. Here, $Ar^1$ may be -Ph-$R^2$ and may be an aryl or heteroaryl group different from $Ar^2$.

In order to prepare a target anthracene derivative, there has been generally used a method of introducing an alkyl group, a cycloalkyl group, a heterocycloalkyl group, an aryl group or a heteroaryl group at position 2 of antracene and then introducing an aryl group or a heteroaryl group at each of positions 9 and 10 of the anthracene. In this case, however, it is difficult to introduce a desired substituent at a specific position of anthracene, thereby resulting in lowered yield. In particular, in the introduction of a substituent at position 2 of anthracene and the introduction of an aryl group or a heteroaryl group at position 9 of the anthracene, selective substitution is difficult, thereby resulting in the production of isomers that are not easily isolated.

The present invention provides a method of preparing a target anthracene derivative in which an alkyl group, a cycloalkyl group, a heterocycloalkyl group, an aryl group or a heteroaryl group is introduced at position 2 of anthracene, and an aryl group or a heteroaryl group is introduced at position 9 of the anthracene, without successive substitution at the positions 2 and 9 of the anthracene, thereby resulting in higher yield.

A preparation method for an anthracene derivative according to the present invention may be represented by Reaction Scheme 1 below:

[Reaction Scheme 1]

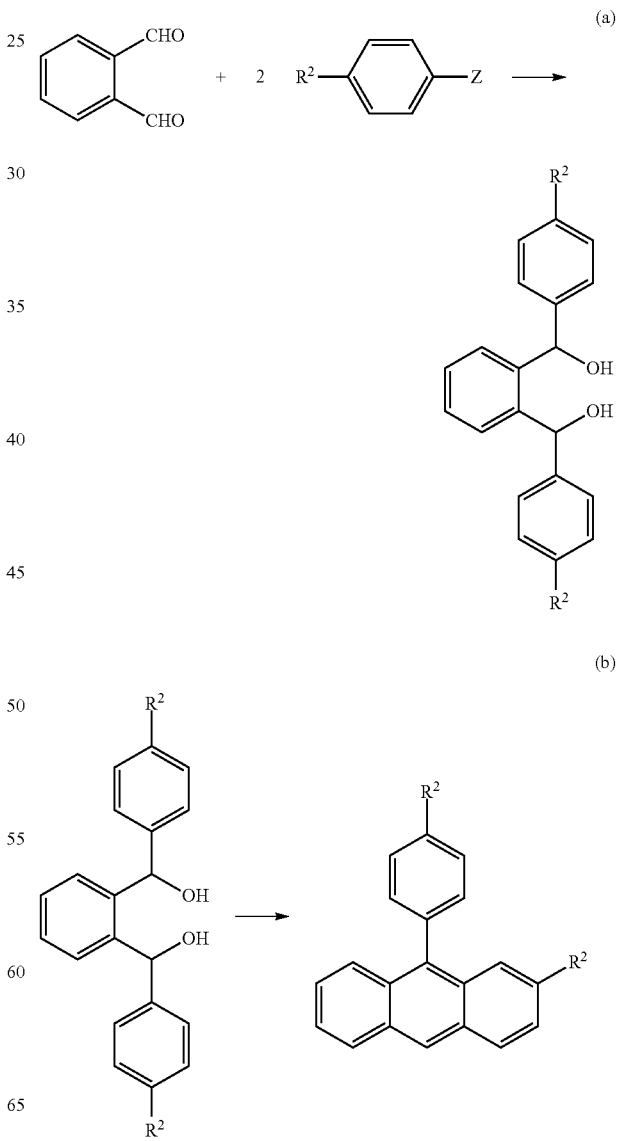

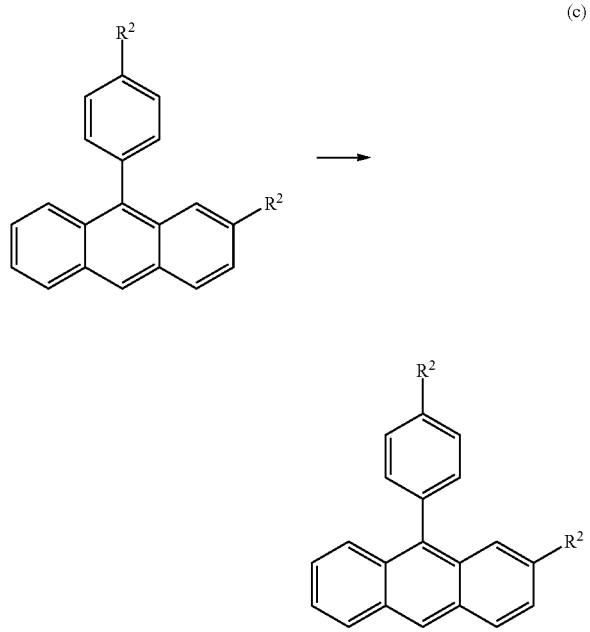

(c)

In step (a), a compound of Formula 1 reacts with a compound of Formula 2 to obtain a compound of Formula 3. At this time, a molar equivalent ratio of the compound of Formula 1 to the compound of Formula 2 may be 1:1~1:10, preferably 1:2.

The compound of Formula 2 is a compound with $R^2$ which is the same functional group (e.g., an alkyl group, an aryl group or a heteroaryl group) as a functional group to be introduced at position 2 of a target anthracene derivative.

Step (a) may be performed at 0 to 50° C. for 1~60 hours in an inert solvent commonly known in the art. Examples of the inert solvent include, but are not limited to, saturated hydrocarbons such as pentane, hexane, heptane, octane, and cyclohexane; ethers such as 1,2-dimethoxyethane, diethylether, methyl-t-butylether, tetrahydrofuran and dioxane; aromatic hydrocarbons such as benzene, toluene, and xylene; and mixtures thereof.

In step (b), the compound of Formula 3 is cyclized to obtain a compound of Formula 4. Owing to step (b), it is possible to introduce an alkyl group, an aryl group or a heteroaryl group at position 2 of anthracene and an aryl group or a heteroaryl group at position 9 of the anthracene, without successive substitution at the positions 2 and 9, and further, there is no likelihood of formation of isomers.

The cyclization reaction may be performed by a method commonly known in the art. For example, the compound of Formula 3 is acetylated in the presence of acetic anhydride or acetyl halide, followed by reaction in the presence of an acid to thereby produce an anthracene derivative with selective substitution at positions 2 and 9 of anthracene.

In step (c), an aryl group ($Ar_2$) is introduced at position 10 of anthracene of the compound of Formula 4 through a coupling reaction known in the art. In detail, halogen is introduced at the position 10 of the anthracene of the compound of Formula 4, followed by Suzuki coupling reaction, to obtain the compound of Formula 5.

The halogenation reaction may be performed using a halogenating agent known in the art. For example, the halogenating agent may be halosuccinimide (Formula 7 below), a halogen ($F_2$, $Cl_2$, $Br_2$, $I_2$), etc. The halogenating agent may be used in an amount of 0.8 to 10 molar equivalent ratio, preferably 1 to 5 molar equivalent ratio, based on the compound of Formula 4.

[Formula 7]

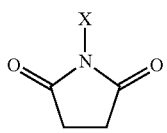

wherein X is a halogen selected from the group consisting of F, Cl, Br and I.

The halogenation reaction may be performed at 0 to 200° C., preferably 20 to 120° C., for 1 to 24 hours in an inert solvent. The inert solvent may be N,N-dimethylformamide, N,N-dimethylacetamide, N-methylpyrrolidone, dimethylsulfoxide, carbon tetrachloride, chlorobenzene, dichlorobenzene, nitrobenzene, toluene, xylene, water or a mixture thereof.

The Suzuki coupling reaction may be performed by a method commonly known in the art. A Suzuki coupling agent that can be used herein may be an aryl-boronic acid of $Ar^2$—$B(OH)_2$.

The Suzuki coupling reaction is generally performed under an atmospheric pressure in the presence of an inert gas such as nitrogen, argon, helium, etc. If necessary, the Suzuki coupling reaction may be performed under a pressurized condition. The Suzuki coupling reaction may be performed at 15~300° C., preferably 30~200° C., for 1~48 hours.

A solvent that can be used in the Suzuki coupling reaction may be water; aromatic hydrocarbons such as benzene, toluene, or xylene; ethers such as 1,2-dimethoxyethane, diethylether, methyl-t-butylether, tetrahydrofuran, or dioxane; saturated hydrocarbons such as pentane, hexane, heptane, octane, or cyclohexane; halogens such as dichloromethene, chloroform, carbon tetrachloride, 1,2-dichloroethene or 1,1,1-trichloroethane; nitriles such as acetonitrile or benzonitrile; esters such as ethylacetic acid, methylacetic acid, or butylacetic acid; amides such as N,N-dimethylformamide, N,N-dimethylacetamide or N-methylpyrrolidone; or mixtures thereof.

A base that can be used in the Suzuki coupling reaction may be sodium carbonate, potassium carbonate, sodium hydroxide, potassium hydroxide, sodium hydrogen carbonate, potassium hydrogen carbonate, magnesium carbonate, lithium carbonate, potassium fluoride, cesium fluoride, cesium chloride, cesium bromide, cesium carbonate, potassium phosphate, methoxysodium, t-butoxypotassium, t-butoxysodium, t-butoxylithium, etc.

A catalyst that can be used in the Suzuki coupling reaction may be a palladium catalyst such as tetrakis(triphenylphosphine)palladium, dichlorobis(triphenylphosphine)palladium, dichloro[bis(diphenylphosphino)ethane]palladium, dichloro[bis(diphenylphosphino)propene]palladium, dichloro[bis(diphenylphosphino)butene]palladium, dichloro[bis(diphenylphosphino)ferrocene]palladium, etc.; a nickel catalyst such as tetrakis(triphenylphosphine)nickel, dichlorobis(triphenylphosphine)nickel, dichloro[bis(diphenylphosphino)ethane]nickel, dichloro[bis(diphenylphosphino)propene]nickel, dichloro[bis(diphenylphosphino)butene]nickel, or dichloro[bis(diphenylphosphino)ferrocene]nickel, etc.

Hereinafter, the present invention will be described more specifically with reference to the following examples. The following examples are only for illustrative purposes and are not intended to limit the scope of the invention.

EXAMPLE 1

Preparation of Target Anthracene Derivative (Cpd 1)

Example 1-1

L, 1.5 M in THF, 1.5 mol) was dropwise added thereto at room temperature. Then, the resultant mixture was stirred at room temperature for one hour, and an aqueous ammonium chloride solution was added thereto to complete the reaction. The reaction solution was extracted with ethyl acetate, dried over magnesium persulfate, and concentrated.

Example 1-2

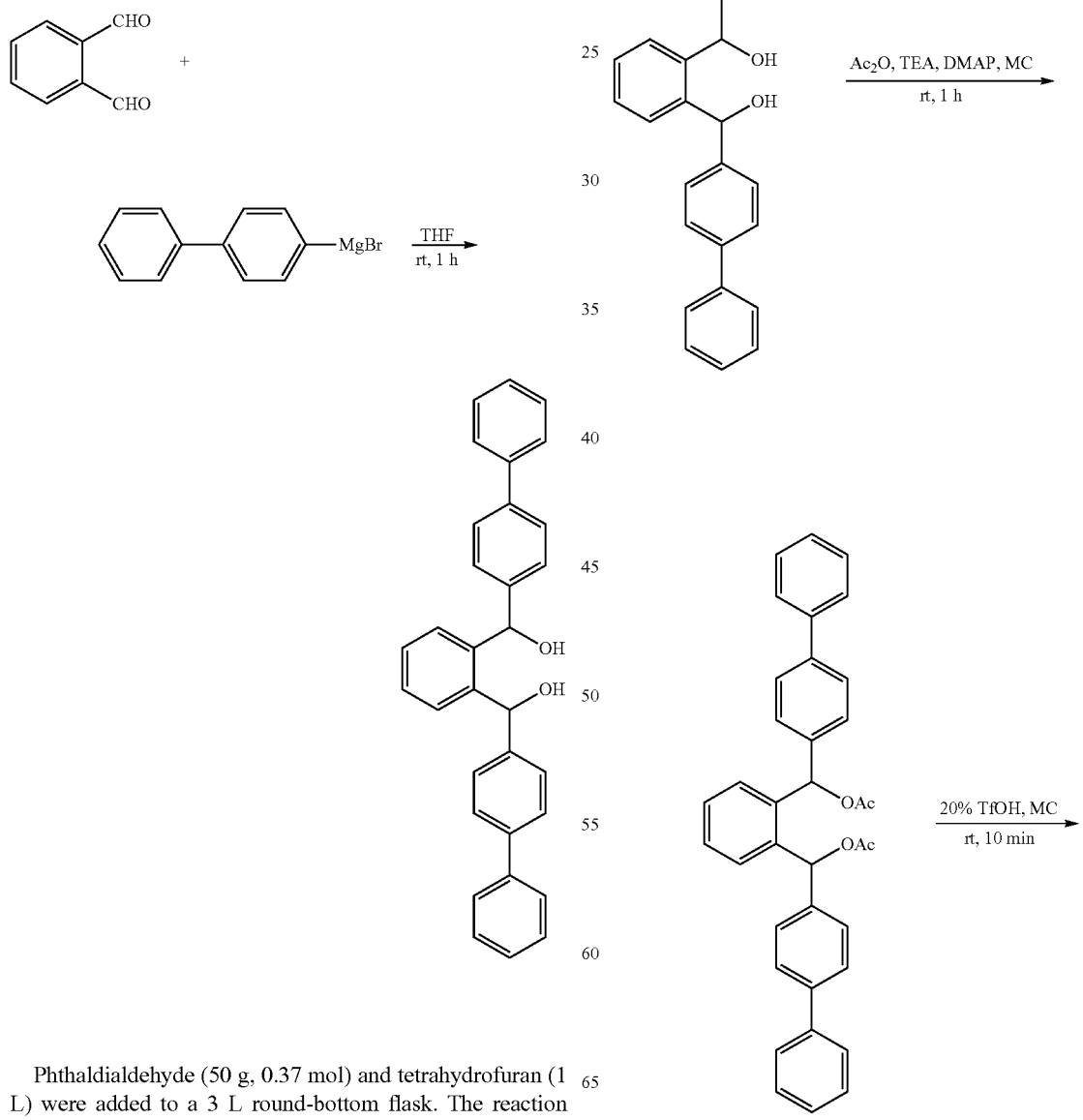

Phthaldialdehyde (50 g, 0.37 mol) and tetrahydrofuran (1 L) were added to a 3 L round-bottom flask. The reaction mixture was stirred, and 4-biphenyl magnesium bromide (1

-continued

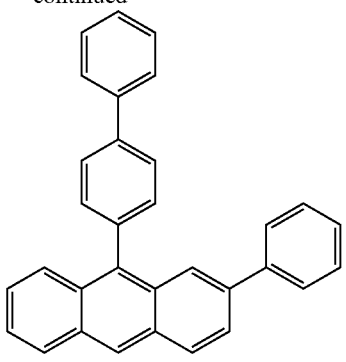

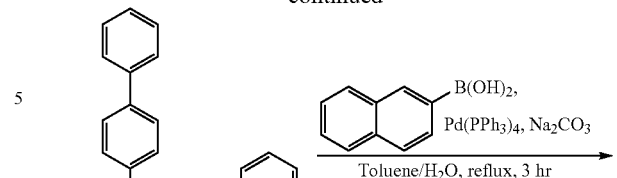

Methylene chloride (1 L) was added to a compound obtained in Example 1-1, followed by stirring. Then, triethylamine (309 ml, 2.22 mol), acetic anhydride (140 ml, 1.48 mol), and dimethylaminopyridine (9 g, 0.074 mol) were added, and the reaction mixture was stirred for one hour. After completing the reaction using an aqueous sodium hydrogen carbonate, the reaction solution was extracted with methylene chloride, dried over sodium sulfate, filtered, concentrated, and recrystallized from methylene chloride and hexane to give a diacetate compound (155 g, yield 80%) as a white solid.

$^1$H NMR (CDCl$_3$): □2.02 (s), 2.08 (s), 7.15-7.51 (m), HRMS for C$_{36}$H$_{30}$O$_4$Na[M+Na]$^+$: calcd 549. Found 549.

The diacetate (150 g, 0.28 mol) thus obtained and trifluoromethanesulfonic acid (4 ml, 0.056 mol) were added to methylene chloride (4 L), and the reaction mixture was stirred at room temperature for 10 minutes and filtered on a silica gel. The filtrate was concentrated and recrystallized from methanol/methylene chloride to give a yellow solid (114 g, yield 82%).

$^1$H NMR (CDCl$_3$): □7.25-7.60 (m, 12H), 7.69-7.80 (m, 6H), 7.95 (s, 1H), 8.00 (d, 1H), 8.07 (d, 1H), 8.46 (s, 1H), HRMS for C$_{32}$H$_{22}$ [M]$^+$: calcd 406. Found 406.

Example 1-3

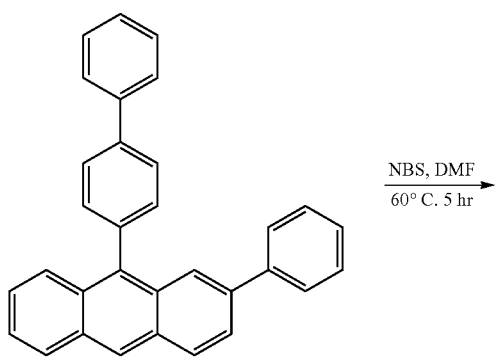

NBS, DMF
60° C. 5 hr

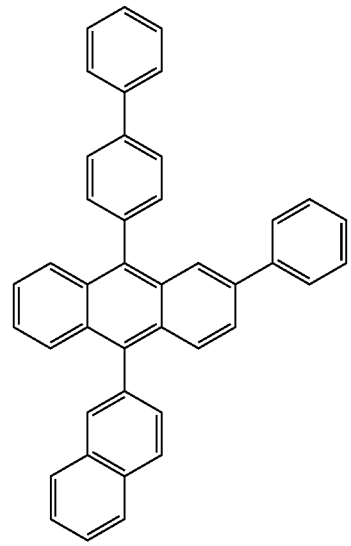

The yellow solid (110 g, 0.27 mol) obtained in Example 1-2 and N-bromosuccinimide (48 g, 0.27 mol) were added to dimethylformamide (1 L), and the reaction mixture was stirred at 60° C. for five hours and cooled to room temperature. The reaction solution was filtered on a silica gel, concentrated, and dried under vacuum.

The resultant compound was dissolved in toluene (1 L) under a nitrogen atmosphere, and 2-naphthalenyl boronic acid (51.6 g, 0.3 mol), tetrakistriphenylphosphine palladium (9.3 g, 8.1 mmol), sodium carbonate (31.4 g, 0.3 mol), and water (300 ml) were added thereto. The reaction mixture was stirred under reflux for three hours. The reaction solution was cooled to about 60° C., filtered on silica gel, and extracted with toluene. The extracted solution was concentrated to remove an organic solvent, and methanol was added thereto. The resultant solid was filtered. The resultant yellowish brown matter was dissolved in methylene chloride, and methanol was dropwise added thereto to give an anthracene derivative (Cpd 1, 122 g, yield 85%) as a pale yellow solid.

The anthracene derivative was identified by mass spectroscopy and NMR (see FIG. 1).

Elemental Analysis for C$_{42}$H$_{28}$: calcd C, 94.70; H, 5.30. Found C, 94.90; H, 5.10. HRMS for C$_{42}$H$_{28}$ [M]$^+$: calcd 532. Found 532.

EXAMPLES 2~24

Preparation of Target Anthracene Derivatives (Cpd 2~Cpd 24)

Anthracene derivatives (Cpd 2~Cpd 24) were prepared in the same manner as in Example 1 except for using compounds presented in Table 1 below instead of 4-biphenyl magnesium bromide of Example 1-1 and 2-naphthalenyl boronic acid of Example 1-3.

TABLE 1
| Grignard reagent | Boronic acid | Anthracene derivative |
|---|---|---|
| Example 1 | | |
| 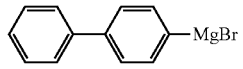 | 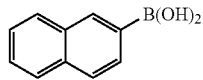 | 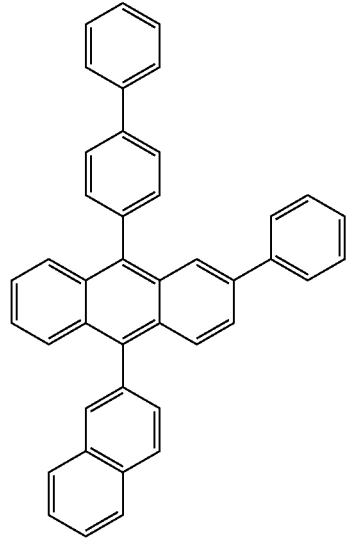<br>Cpd 1 |
| Example 2 | | |
| 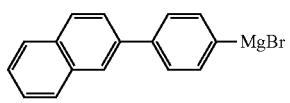 | 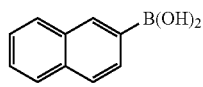 | 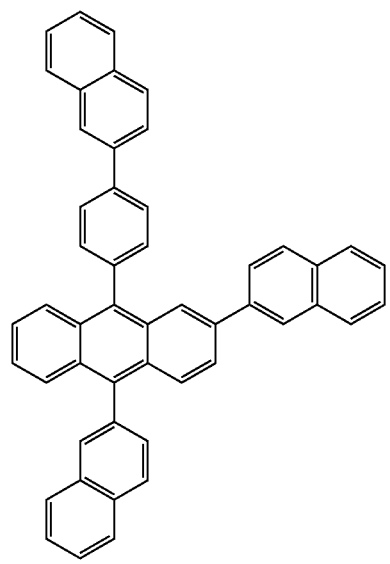<br>Cpd 2 |

TABLE 1-continued
| Grignard reagent | Boronic acid | Anthracene derivative |
|---|---|---|
Example 3
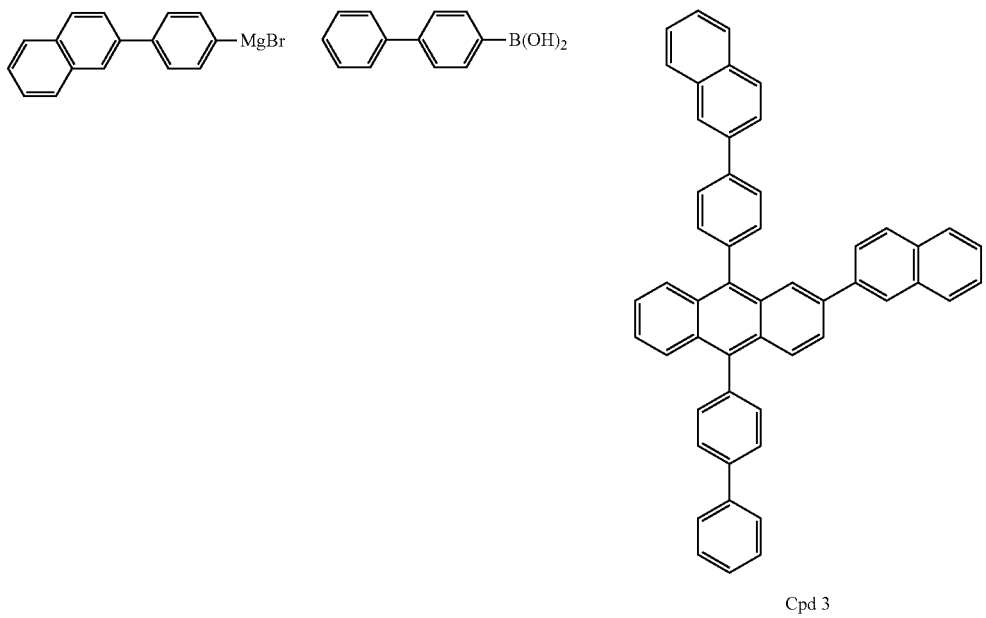
Cpd 3
Example 4
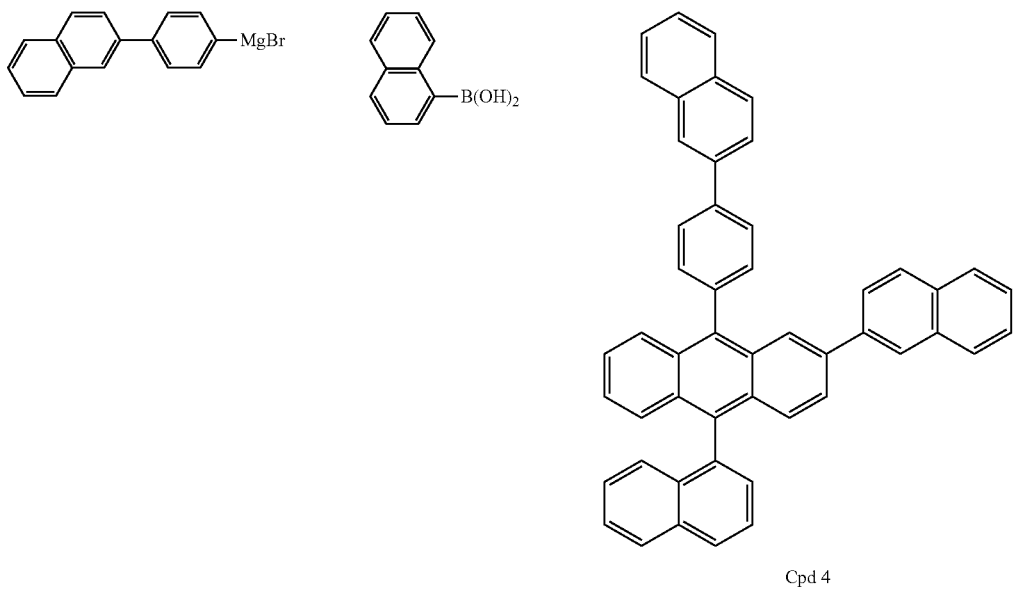
Cpd 4

TABLE 1-continued
| Grignard reagent | Boronic acid | Anthracene derivative |
|---|---|---|
Example 5
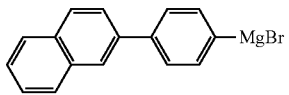 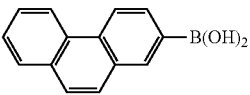 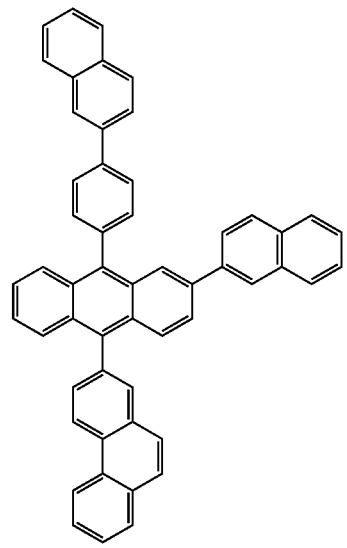
Cpd 5
Example 6
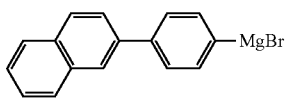 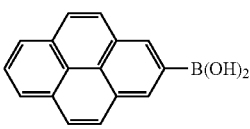 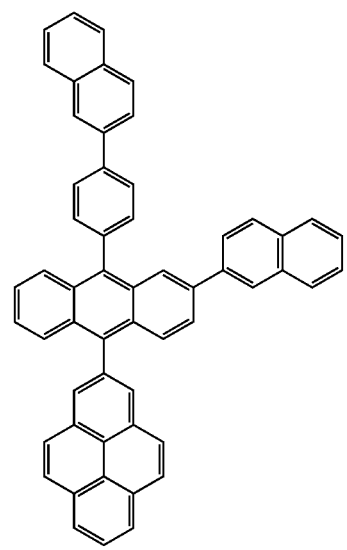
Cpd 6

TABLE 1-continued
| Grignard reagent | Boronic acid | Anthracene derivative |
|---|---|---|
Example 7
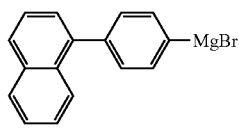 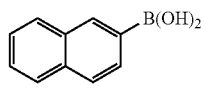 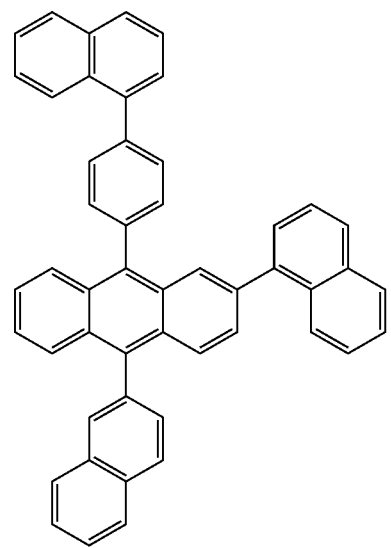
Cpd 7
Example 8
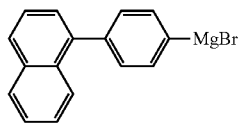 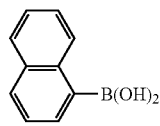 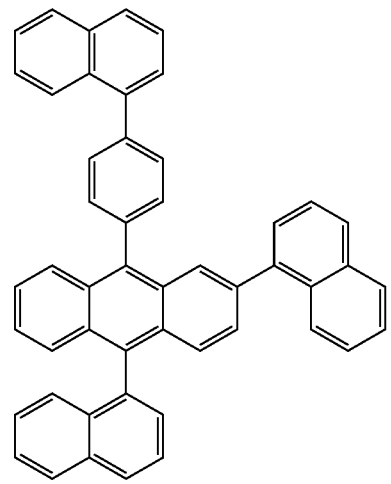
Cpd 8

TABLE 1-continued
| Grignard reagent | Boronic acid | Anthracene derivative |
| --- | --- | --- |
Example 9
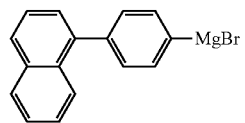 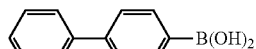 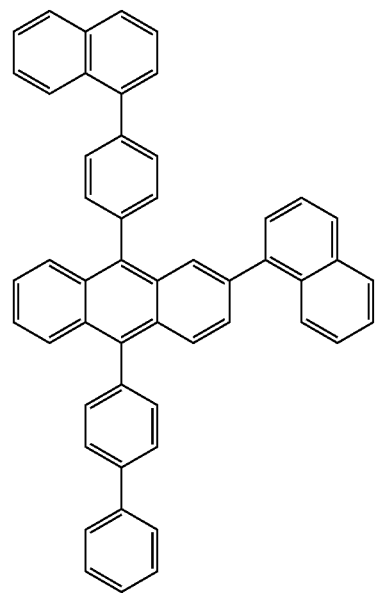
Cpd 9
Example 10
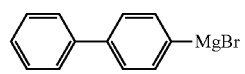 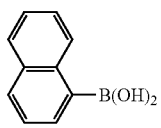 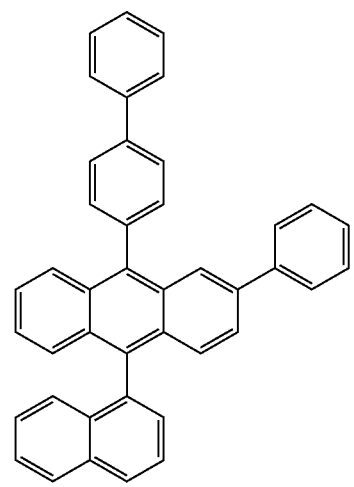
Cpd 10

TABLE 1-continued
| Grignard reagent | Boronic acid | Anthracene derivative |
| --- | --- | --- |
Example 11
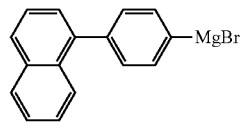 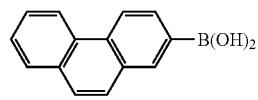 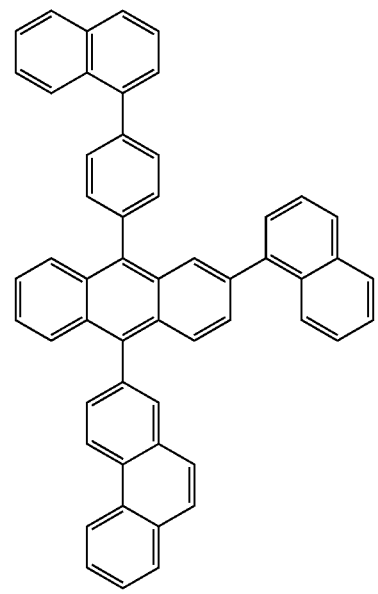
Cpd 11
Example 12
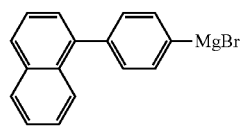 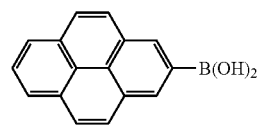 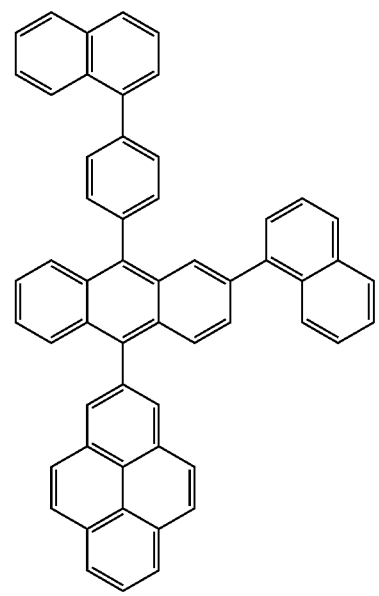
Cpd 12

TABLE 1-continued
| Grignard reagent | Boronic acid | Anthracene derivative |
| --- | --- | --- |
Example 13
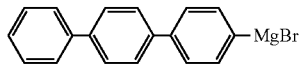 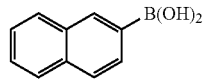 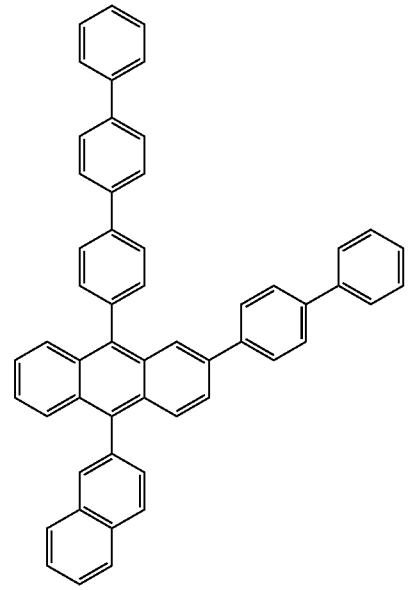
Cpd 13
Example 14
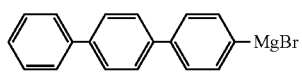 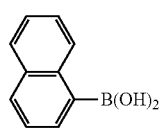 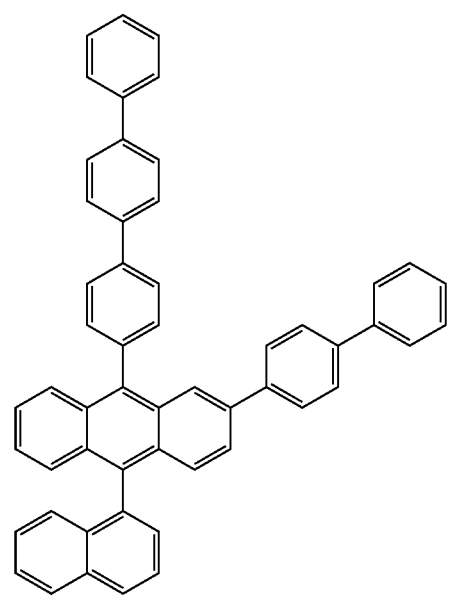
Cpd 14

TABLE 1-continued

| | Grignard reagent | Boronic acid | Anthracene derivative |
|---|---|---|---|
| Example 15 | 4-([1,1':4',1''-terphenyl]-4-yl)MgBr | [1,1'-biphenyl]-4-yl-B(OH)$_2$ | Cpd 15 |
| Example 16 | t-Bu-C$_6$H$_4$-MgBr | naphthalen-1-yl-B(OH)$_2$ | Cpd 16 |
| Example 17 | t-Bu-C$_6$H$_4$-MgBr | naphthalen-2-yl-B(OH)$_2$ | Cpd 17 |

TABLE 1-continued
| Grignard reagent | Boronic acid | Anthracene derivative |
| --- | --- | --- |
Example 18
 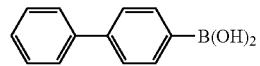 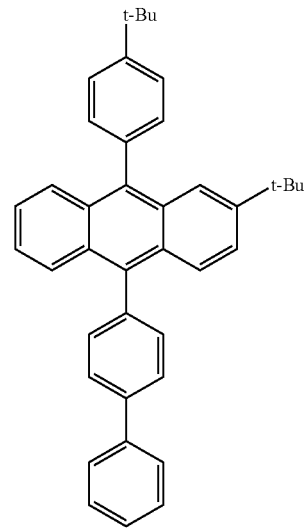
Cpd 18
Example 19
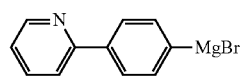 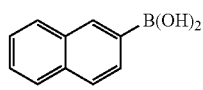 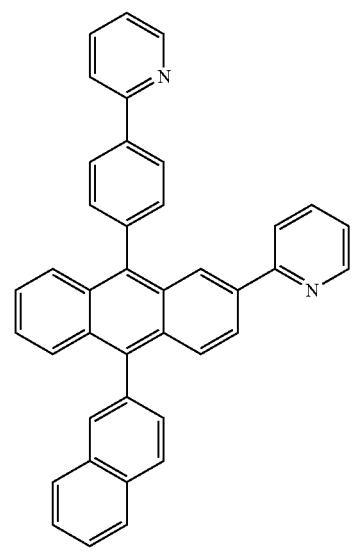
Cpd 19

TABLE 1-continued
| Grignard reagent | Boronic acid | Anthracene derivative |
|---|---|---|
Example 20
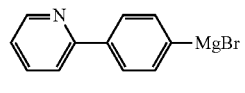 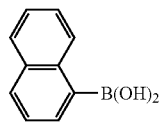 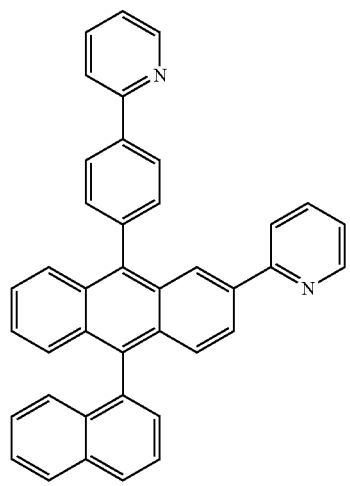
Cpd 20
Example 21
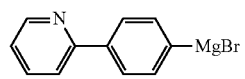 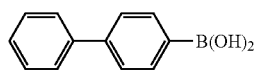 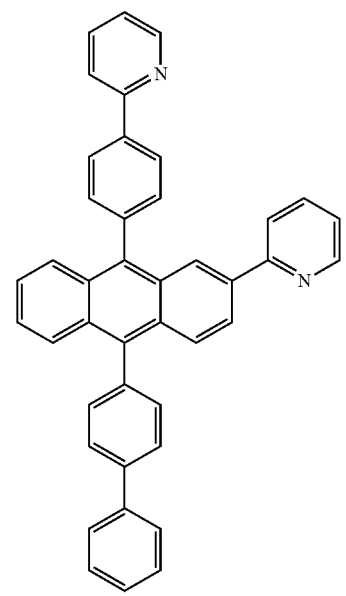
Cpd 21

TABLE 1-continued
| Grignard reagent | Boronic acid | Anthracene derivative |
| --- | --- | --- |
Example 22
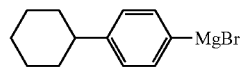 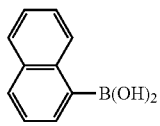 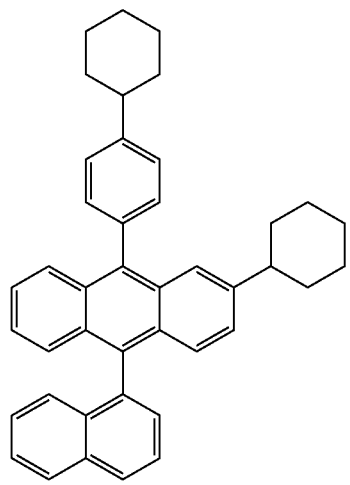
Cpd 22
Example 23
Cpd 23

TABLE 1-continued

| | Grignard reagent | Boronic acid | Anthracene derivative |
|---|---|---|---|
| Example 24 | 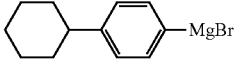 | 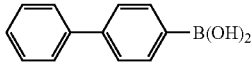 | 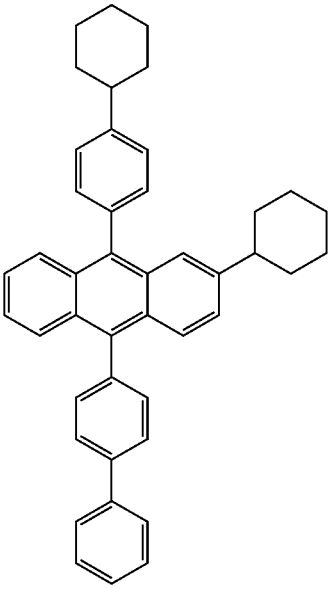
Cpd 24 |

Figure 2:
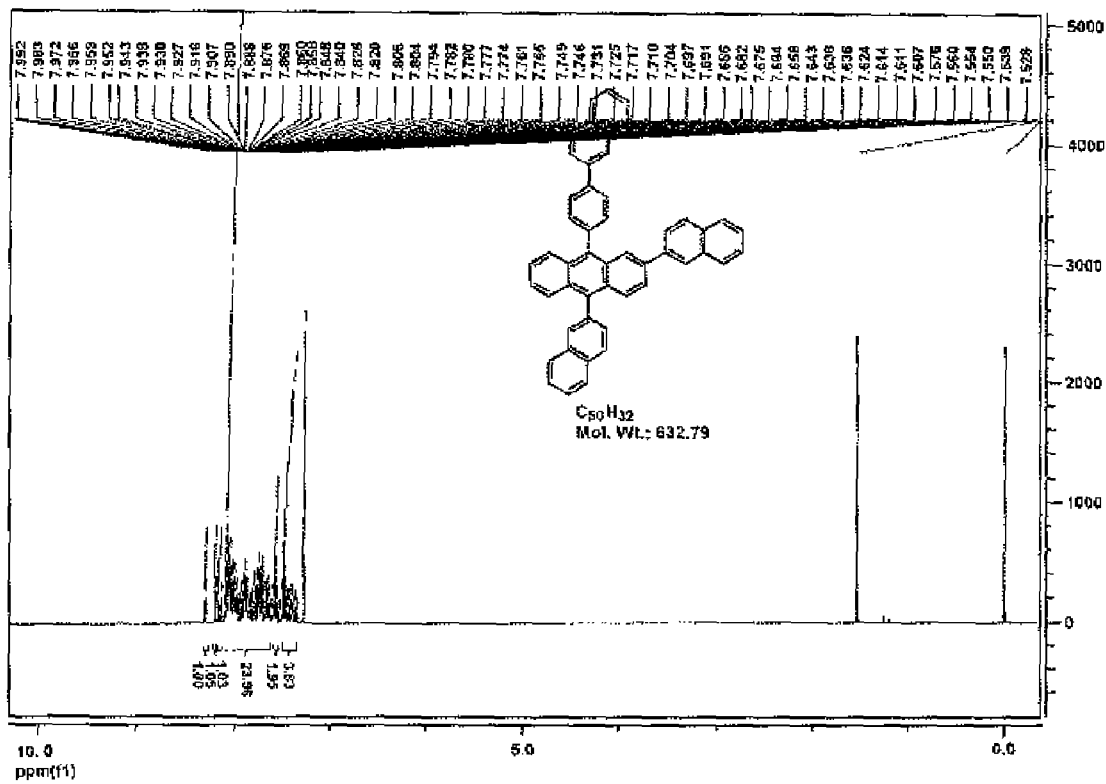
FIG. 2 is an NMR spectrum for an anthracene derivative (Cpd 2) of Example 2.
Figure 2:
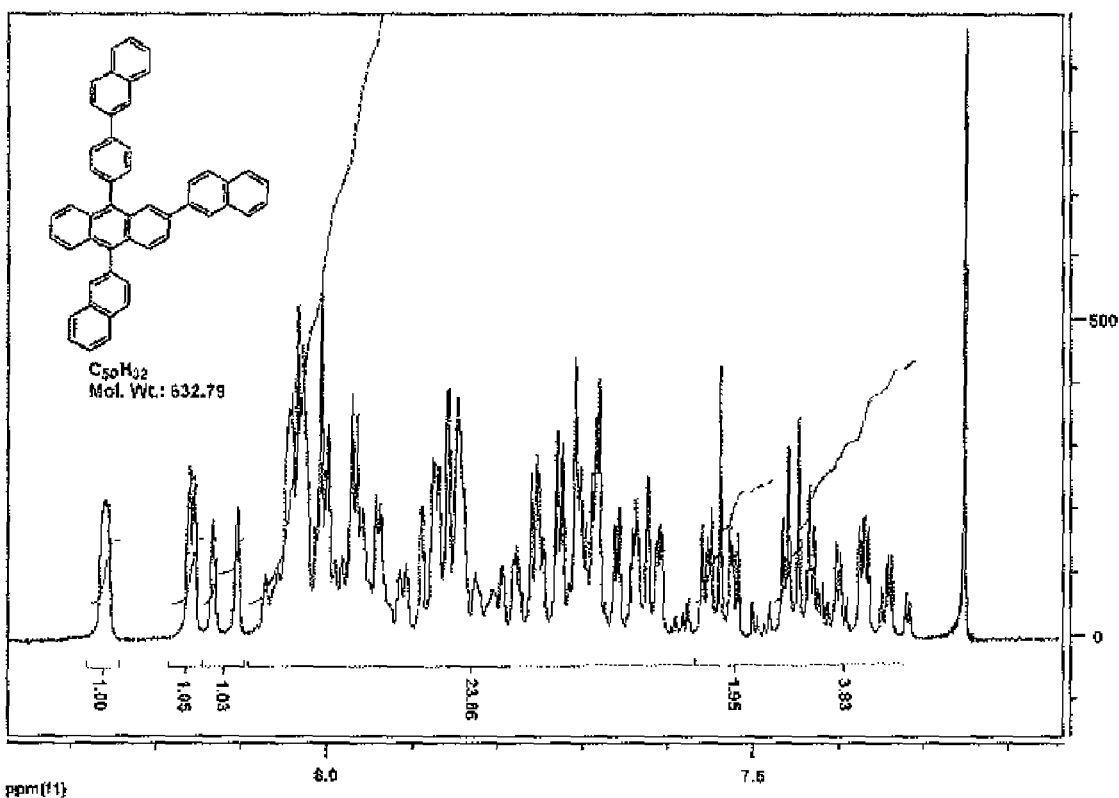
Figure 3:
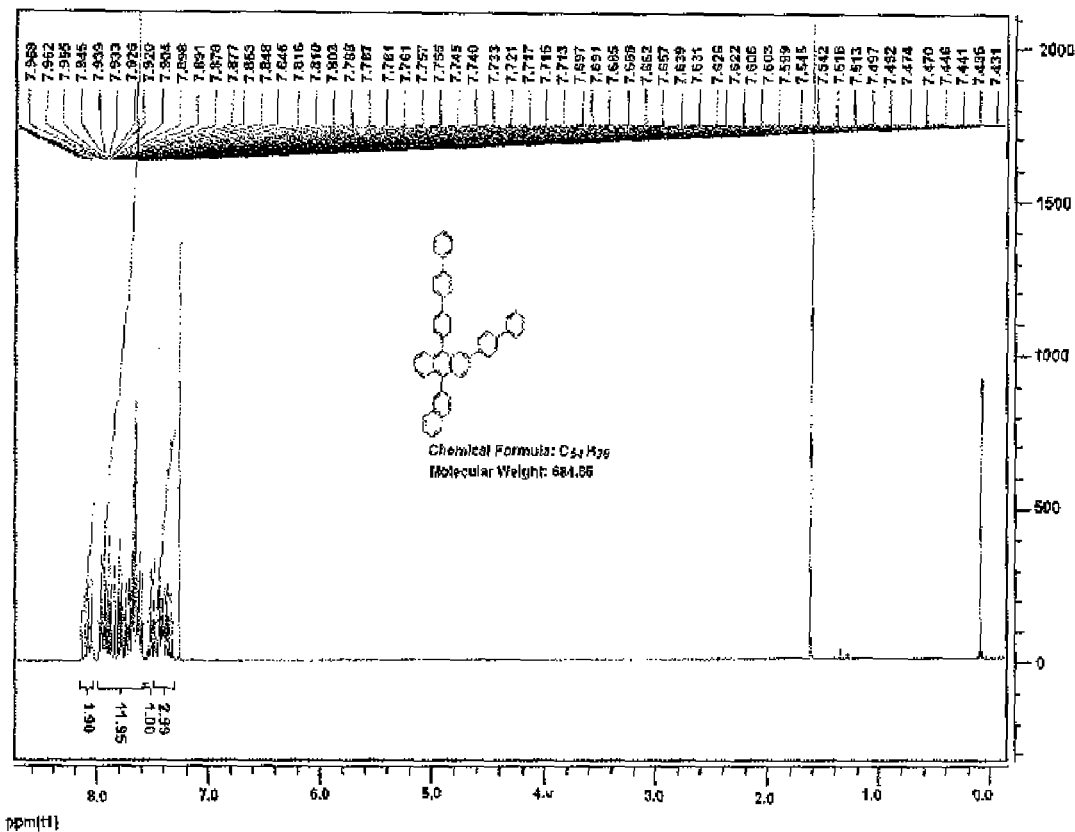
FIG. 3 is an NMR spectrum for an anthracene derivative (Cpd 3) of Example 3.
Figure 3:
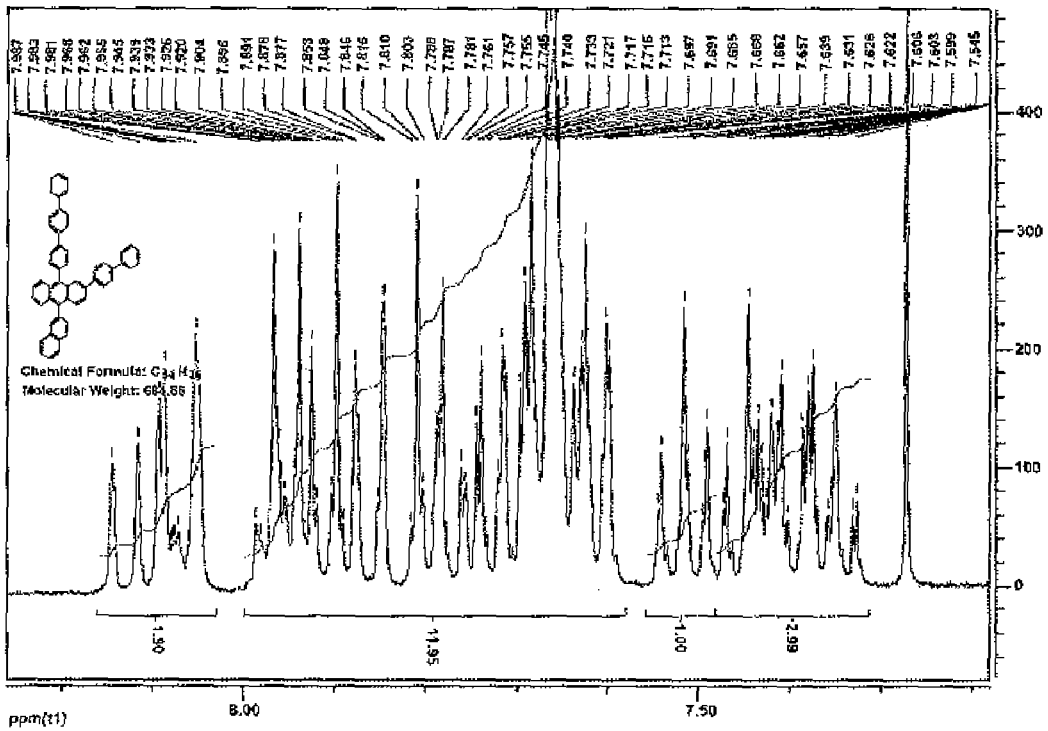

Among these anthracene derivatives, NMR analysis was performed for Cpd 2 of Example 2 and Cpd 13 of Example 13. The results are shown in FIGS. 2 and 3.

EXPERIMENTAL EXAMPLE 1

Evaluation of Performance for OLEDs

OLEDs were manufactured by the following method.

DS-205 (Doosan, Korea) was deposited under thermal vacuum to a thickness of 800 Å on an ITO (Indium tin oxide; anode) substrate to form a hole injection layer. NPB (N,N-di(naphthalene-1-yl)-N, N-diphenylbenzidine) was deposited under vacuum to a thickness of 150 Å on the hole injection layer to form a hole transport layer. Each of the anthracene derivatives (Cpd 1~Cpd 24) of Examples 1 to 24 was doped with a compound of Formula 8 below (5%), and the resultant material was deposited under vacuum to a thickness of 300 Å on the hole transport layer to form a light-emitting layer. An electron transport material, $Alq_3$ was deposited under vacuum to a thickness of 250 Å on the light-emitting layer. Then, an electron injection material, LiF was deposited to a thickness of 10 Å, and aluminum (cathode) was deposited under vacuum to a thickness of 2000 Å to thereby complete OLEDs.

[Formula 8]

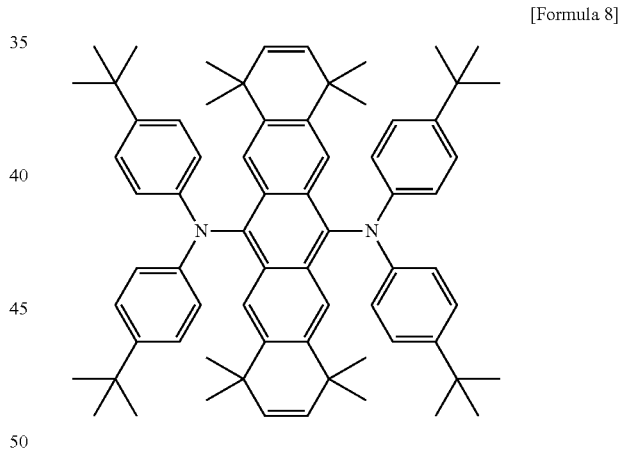

For the OLEDs thus manufactured, emission efficiencies at current density of 10 $mA/cm^2$ were measured. The results are summarized in Table 2 below.

TABLE 2

| | Anthracene derivative | Driving voltage (V) | Emission efficiency (cd/A) |
|---|---|---|---|
| Example 1 | Cpd 1 | 7.0 | 18 |
| Example 2 | Cpd 2 | 6.1 | 24 |
| Example 3 | Cpd 3 | 6.3 | 22 |
| Example 4 | Cpd 4 | 6.7 | 22 |
| Example 5 | Cpd 5 | 6.5 | 18 |
| Example 6 | Cpd 6 | 6.9 | 23 |
| Example 7 | Cpd 7 | 6.2 | 19 |
| Example 8 | Cpd 8 | 6.4 | 18 |
| Example 9 | Cpd 9 | 6.8 | 22 |

TABLE 2-continued

| | Anthracene derivative | Driving voltage (V) | Emission efficiency (cd/A) |
|---|---|---|---|
| Example 10 | Cpd 10 | 6.8 | 17 |
| Example 11 | Cpd 11 | 6.6 | 16 |
| Example 12 | Cpd 12 | 6.2 | 20 |
| Example 13 | Cpd 13 | 6.5 | 19 |
| Example 14 | Cpd 14 | 6.3 | 21 |
| Example 15 | Cpd 15 | 6.3 | 23 |
| Example 16 | Cpd 16 | 7.3 | 14 |
| Example 17 | Cpd 17 | 7.2 | 13 |
| Example 18 | Cpd 18 | 7.0 | 16 |
| Example 22 | Cpd 22 | 7.5 | 13 |
| Example 23 | Cpd 23 | 7.1 | 16 |
| Example 24 | Cpd 24 | 6.9 | 15 |

When using the anthracene derivatives prepared by the inventive method as light-emitting hosts of OLEDs, all the OLEDs exhibited high brightness. In particular, the OLED using the anthracene derivative of Example 2 exhibited a low driving voltage, high brightness, and excellent lifetime performance (200 hours were required for 10% reduction in brightness at 9000 nit). Such a lifetime performance is greater than that (180 hours are required for 10% reduction in brightness at 9000 nit) of a conventional OLED using TNA (2,9,10-tri(naphthalen-2-yl)anthracene) as a light-emitting host.

What is claimed is:

1. A method of preparing an anthracene derivative represented by Formula 5 below, the method comprising:
   (a) reacting a compound of Formula 1 below with a compound of Formula 2 below to obtain a compound of Formula 3 below;
   (b) cyclizing the compound of Formula 3 to obtain a compound of Formula 4 below; and
   (c) introducing an aryl group at position 10 of anthracene of the compound of Formula 4,

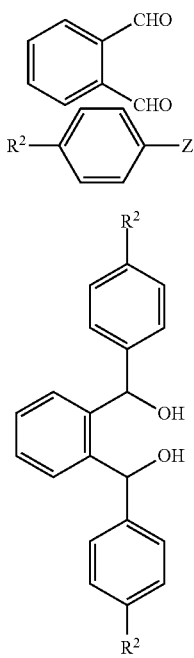

[Formula 1]

[Formula 2]

[Formula 3]

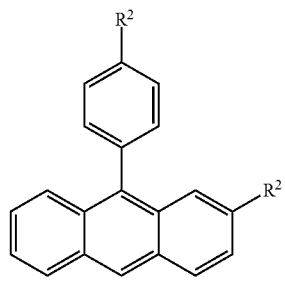

[Formula 4]

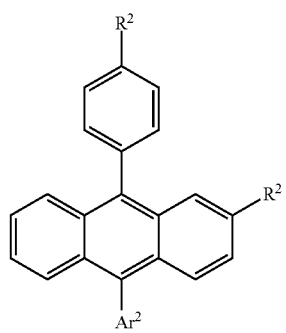

[Formula 5]

wherein Z is MgX where X is halogen, Li, or Na; $R^2$ is an alkyl group of $C_1$~$C_{30}$, a cycloalkyl group of $C_5$~$C_{30}$, a heterocycloalkyl group of $C_5$~$C_{30}$, an aryl group of $C_5$~$C_{30}$, or a heteroaryl group of $C_5$~$C_{30}$; $Ar^2$ is an aryl group of $C_5$~$C_{30}$ or a heteroaryl group of $C_5$~$C_{30}$; and wherein the alkyl group, cycloalkyl group, heterocycloalkyl group, aryl group and heteroaryl group are each independently unsubstituted or substituted by at least one selected from the group consisting of $C_1$-$C_{30}$ alkyl, $C_2$-$C_{30}$ alkenyl, $C_2$-$C_{30}$ alkynyl, $C_5$-$C_{30}$ aryl, $C_5$-$C_{30}$ heteroaryl, $C_5$-$C_{30}$ aryloxy, $C_1$-$C_{30}$ alkyloxy, $C_5$-$C_{30}$ arylamino, $C_5$-$C_{30}$ diarylamino, $C_5$-$C_{30}$ arylalkyl, $C_5$-$C_{30}$ cycloalkyl, $C_5$-$C_{30}$ heterocycloalkyl and a halogen atom.

2. The method of claim 1, wherein in step (b), the compound of Formula 3 is acetylated and cyclized.

3. The method of claim 1, wherein in step (c), a halogen is introduced at position 10 of the anthracene of the compound of Formula 4 and the resultant compound is subjected to Suzuki coupling reaction with $Ar^2$—$B(OH)_2$ to obtain the compound of Formula 5.

* * * * *